US005712121A

United States Patent [19]
Devos et al.

[11] Patent Number: 5,712,121
[45] Date of Patent: *Jan. 27, 1998

[54] CHIMERIC INTERLEUKIN 5-RECEPTOR/ IMMUNOGLOBULIN POLYPEPTIDES

[75] Inventors: Rene Devos, Oostende; Walter Fiers, Destelbergen; Jose van der Heyden, Munte; Geert Plaetinck, Destelbergen; Jan Tavernier, Balegem, all of Belgium

[73] Assignee: Hoffmann-La Roche Inc., Nutley, N.J.

[*] Notice: The term of this patent shall not extend beyond the expiration date of Pat. No. 5,455,337.

[21] Appl. No.: 421,823

[22] Filed: Apr. 13, 1995

Related U.S. Application Data

[62] Division of Ser. No. 947,130, Sep. 16, 1992, Pat. No. 5,455,337.

[30] Foreign Application Priority Data

Sep. 18, 1991 [EP] European Pat. Off. .......... 91.810738.4

[51] Int. Cl.$^6$ .................. C07K 14/00; C12N 5/10; C12N 15/11; C12N 15/64
[52] U.S. Cl. .................. 435/69.7; 435/172.3; 435/252.3; 435/320.1; 435/325; 536/23.4; 536/23.5; 536/23.53
[58] Field of Search .................. 536/23.4, 23.5, 536/23.53; 435/69.1, 69.52, 69.7, 172.3, 240.1, 252.3, 320.1, 325

[56] References Cited

U.S. PATENT DOCUMENTS 5,455,337  10/1995  Devos et al. .......................... 536/23.4

FOREIGN PATENT DOCUMENTS

| | | |
|---|---|---|
| 325 262 | 7/1989 | European Pat. Off. . |
| 305 967 | 10/1989 | European Pat. Off. . |
| 394 827 | 4/1990 | European Pat. Off. . |
| 417 563 | 8/1990 | European Pat. Off. . |
| 464 533 | 6/1991 | European Pat. Off. . |
| 475 746 | 9/1991 | European Pat. Off. . |
| 91/08298 | 6/1991 | WIPO . |

OTHER PUBLICATIONS

Devos et al. 1993. J. Biol. Chem. 268:6581–6587.
Bowie et al. 1990. Science 247:1306–1310.
Aruffo and Seed, Proc. Natl. Acad. Sci. USA 84, 8573 (1987).
Birnboim and Doly, Nucl. Acids. Res. 7, 1513 (1979).
Clutterbuck et al., Eur. J. Immunol. 17, 1743–1750 (1987).
Cullen, Cell, 46, 973–982 (1986).
Felgner et al., Proc. Natl. Acad. Sci. USA 84, 7413–7417 (1987).
German, C., "DNA Cloning" (vol. II., edt. by Glover, D.M., IRL Press, Oxford, 1985) (book—copy not enclosed).
Huck et al., Nucl. Acids Res. 14, 1779–1789 (1986).
Lopez et al., J. Exp. Med. 167, 219–224 (1988).
Malizewski and Fanslow, Tibtech., 8, 324–329 (1990).
Maniatis, T., Fritsch, E.R. and Sambrook, J., "Molecular Cloning", Cold Spring Harbor Lab. Press, USA (1982) (book—copy not enclosed).
Neurath, H. and Hill, R.L. in "The Proteins", Academic Press, N.Y., 14 (1979) (book—copy not enclosed).
Plaetinck et al., J. Exp. Med. 172, 683–691 (1990).
Rolink et al., J. Exp. Med. 169, 1693–1701 (1989).
Sambrook et al., "Molecular Cloning", 2nd ed., Cold Spring Harbor Laboratory Press, USA (1989) (book—copy not enclosed).
Seed, Nature, 329, 840 (1987).
Seed and Aruffo, Proc. Natl. Acad. Sci. USA, 84, 3365 (1987).
Sharma, S. et al. in "Current Communications in Molecular Biology", edt. by Gething, M.J., Cold Spring Harbor Lab. Press USA (1985) (book—copy not enclosed.
Traunecker et al., Nature 331, 84–86 (1988).
Yamaguchi et al., International Immunology 2, 181–187 (1990).
Takaki, S. et al., EMBO Journal, vol. 9, No. 13, pp. 4367–4374 (1990).
Patent Abstracts of Japan—JP-A-10 63 394, vol. 13, No. 262 (1989).
Takaki et al., Lymphokine Research, vol. 9, No. 4, pp. 572–S7.4 (1990).
The Journal of Experimental Medicine, vol. 172, No. 3, pp. 683–691 (1990).
Derwent Abstract No. 91–081851/12 92–009794/02.
Robinson, D.S., Clinical and Experimental Allergy, 23:1–3 (1993).
Corrigan, et al., Am. Rev. Respir. Dis., 147:540–547 (1993).
Mauser, et al., Am. Rev. Respir. Dis., 148:1623–1627 (1993).
Devos, et al., J. Bio. Chem., 268:6581–6587 (1992).
Gross, et al., Proc. Natl. Acad. Sci., 86:10024–10028 (1989).
Murata, et al., J. Exp. Med., 175:341–351 (1992).

*Primary Examiner*—David L. Fitzgerald
*Assistant Examiner*—Elizabeth C. Kemmerer
*Attorney, Agent, or Firm*—George W. Johnston; William H. Epstein; Lewis J. Kreisler

[57] ABSTRACT

Chimeric polypeptides encoded by a DNA sequence having a first DNA subsequence coding for a fragment of at least one of the α-and/or β-chain of the human interleukin-5 receptor, and a second DNA subsequence coding for the constant domains of a heavy—or a light-chain of a human immunoglobulin, or a fragment thereof are useful in treating illnesses with demonstrated eosinophilia.

27 Claims, 2 Drawing Sheets

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
      ( A ) LENGTH: 1351 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Homo sapiens
      ( F ) TISSUE TYPE: leukemia
      ( G ) CELL TYPE: promyelocytes
      ( H ) CELL LINE: HL-60

( v i i ) IMMEDIATE SOURCE:
      ( A ) LIBRARY: human HL-60
      ( B ) CLONE: lambda gt11- hIL5Ralpha12

( x i ) SEQUENCE DESCRIPTION: SEQ ID NO:1:

```
CCGCTGCTTC   TCATCGCATG   GCCACCGCAT   TTCTCAGGCC   AGGCACATTG   AGCATTGGTC        60

CTGTGCCTGA   CGCTATGCTA   GATGCTGGGG   TTGCAGCCAC   GAGCATAGAC   ACGACAGACA       120

CGGTCCTCGC   CATCTTCTGT   TGAGTACTGG   TCGGAACAAG   AGGATCGTCT   GTAGACAGGC       180

TACAGATTGT   TTTAGATTGA   AGTTTCCTGT   CATGTTCACT   CATCTTTAAA   TCCTCATAGT       240

AAAAAGGATA   TGATCATCGT   GGCGCATGTA   TTACTCATCC   TTTTGGGGGC   CACTGAGATA       300

CTGCAAGCTG   ACTTACTTCC   TGATGAAAAG   ATTTCACTTC   TCCCACCTGT   CAATTTCACC       360

ATTAAAGTTA   CTGGTTTGGC   TCAAGTTCTT   TTACAATGGA   AACCAAATCC   TGATCAAGAG       420
```

| | | | | | |
|---|---|---|---|---|---|
| CAAAGGAATG | TTAATCTAGA | ATATCAAGTG | AAAATAAACG | CTCCAAAAGA | AGATGACTAT | 480 |
| GAAACCAGAA | TCACTGAAAG | CAAATGTGTA | ACCATCCTCC | ACAAGGCTT | TTCAGCAAGT | 540 |
| GTGCGGACCA | TCCTGCAGAA | CGACCACTCA | CTACTGGCCA | GCAGCTGGGC | TTCTGCTGAA | 600 |
| CTTCATGCCC | CACCAGGGTC | TCCTGGAACC | TCAATTGTGA | ATTTAACTTG | CACCACAAAC | 660 |
| ACTACAGAAG | ACAATTATTC | ACGTTAAGG | TCATACCAAG | TTTCCCTTCA | CTGCACCTGG | 720 |
| CTTGTTGGCA | CAGATGCCCC | TGAGGACACG | CAGTATTTTC | TCTACTATAG | GTATGGCTCT | 780 |
| TGGACTGAAG | AATGCCAAGA | ATACAGCAAA | GACACACTGG | GGAGAAATAT | CGCATGCTGG | 840 |
| TTTCCCAGGA | CTTTTATCCT | CAGCAAAGGG | CGTGACTGGC | TTTCGGTGCT | TGTTAACGGC | 900 |
| TCCAGCAAGC | ACTCTGCTAT | CAGGCCCTTT | GATCAGCTGT | TTGCCCTTCA | CGCCATTGAT | 960 |
| CAAATAAATC | CTCCACTGAA | TGTCACAGCA | GAGATTGAAG | GAACTCGTCT | CTCTATCCAA | 1020 |
| TGGGAGAAAC | CAGTGTCTGC | TTTTCCAATC | CATTGCTTTG | ATTATGAAGT | AAAAATACAC | 1080 |
| AATACAAGGA | ATGGATATTT | GCAGATAGAA | AAATTGATGA | CCAATGCATT | CATCTCAATA | 1140 |
| ATTGATGATC | TTTCTAAGTA | CGATGTTCAA | GTGAGAGCAG | CAGTGAGCTC | CATGTGCAGA | 1200 |
| GAGGCAGGGC | TCTGGAGTGA | GTGGAGCCAA | CCTATTTATG | TGGGGTTCTC | AAGATAAAGG | 1260 |
| AGATAACATC | CAGCTTTCCT | GCCCCACACC | GTATCTGAAA | TAAAAACAAC | AGCAGGGATA | 1320 |
| GCAGATTAAA | AAAAAAAAAA | AAAAAAAAA A | | | | 1351 |

( 2 ) INFORMATION FOR SEQ ID NO:2:

( i ) SEQUENCE CHARACTERISTICS:
        ( A ) LENGTH: 335 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens
        ( F ) TISSUE TYPE: leukemia
        ( G ) CELL TYPE: Promyelocytes
        ( H ) CELL LINE: HL-60

( v i i ) IMMEDIATE SOURCE:
        ( A ) LIBRARY: human HL-60
        ( B ) CLONE: lambda gt11- hIL5Ralpha12

( x i ) SEQUENCE DESCRIPTION: SEQ ID NO:2:

```
Met Ile Ile Val Ala His Val Leu Leu Ile Leu Leu Gly Ala Thr Glu
  1               5                  10                  15

Ile Leu Gln Ala Asp Leu Leu Pro Asp Glu Lys Ile Ser Leu Leu Pro
             20                  25                  30

Pro Val Asn Phe Thr Ile Lys Val Thr Gly Leu Ala Gln Val Leu Leu
             35                  40                  45

Gln Trp Lys Pro Asn Pro Asp Gln Glu Gln Arg Asn Val Asn Leu Glu
     50                  55                  60

Tyr Gln Val Lys Ile Asn Ala Pro Lys Glu Asp Asp Tyr Glu Thr Arg
 65                  70                  75                  80

Ile Thr Glu Ser Lys Cys Val Thr Ile Leu His Lys Gly Phe Ser Ala
                 85                  90                  95

Ser Val Arg Thr Ile Leu Gln Asn Asp His Ser Leu Leu Ala Ser Ser
            100                 105                 110
```

```
Trp Ala Ser Ala Glu Leu His Ala Pro Pro Gly Ser Pro Gly Thr Ser
        115                 120                 125
Ile Val Asn Leu Thr Cys Thr Thr Asn Thr Thr Glu Asp Asn Tyr Ser
        130                 135                 140
Arg Leu Arg Ser Tyr Gln Val Ser Leu His Cys Thr Trp Leu Val Gly
145                 150                 155                 160
Thr Asp Ala Pro Glu Asp Thr Gln Tyr Phe Leu Tyr Tyr Arg Tyr Gly
                165                 170                 175
Ser Trp Thr Glu Glu Cys Gln Glu Tyr Ser Lys Asp Thr Leu Gly Arg
                180                 185                 190
Asn Ile Ala Cys Trp Phe Pro Arg Thr Phe Ile Leu Ser Lys Gly Arg
            195                 200                 205
Asp Trp Leu Ser Val Leu Val Asn Gly Ser Ser Lys His Ser Ala Ile
        210                 215                 220
Arg Pro Phe Asp Gln Leu Phe Ala Leu His Ala Ile Asp Gln Ile Asn
225                 230                 235                 240
Pro Pro Leu Asn Val Thr Ala Glu Ile Glu Gly Thr Arg Leu Ser Ile
                245                 250                 255
Gln Trp Glu Lys Pro Val Ser Ala Phe Pro Ile His Cys Phe Asp Tyr
            260                 265                 270
Glu Val Lys Ile His Asn Thr Arg Asn Gly Tyr Leu Gln Ile Glu Lys
            275                 280                 285
Leu Met Thr Asn Ala Phe Ile Ser Ile Ile Asp Asp Leu Ser Lys Tyr
        290                 295                 300
Asp Val Gln Val Arg Ala Ala Val Ser Ser Met Cys Arg Glu Ala Gly
305                 310                 315                 320
Leu Trp Ser Glu Trp Ser Gln Pro Ile Tyr Val Gly Phe Ser Arg
                325                 330                 335
```

( 2 ) INFORMATION FOR SEQ ID NO:3:

( i ) SEQUENCE CHARACTERISTICS:
( A ) LENGTH: 335 amino acids
( B ) TYPE: amino acid
( D ) TOPOLOGY: linear ( i i ) MOLECULE TYPE: protein ( i i i ) HYPOTHETICAL: YES ( v i ) ORIGINAL SOURCE:
( A ) ORGANISM: mouse
( G ) CELL TYPE: B-cell precursor
( H ) CELL LINE: B13

( x i ) SEQUENCE DESCRIPTION: SEQ ID NO:3:

```
Xaa Xaa Xaa Met Val Pro Val Leu Leu Ile Leu Val Gly Ala Leu Ala
1               5                   10                  15
Thr Leu Gln Ala Asp Leu Leu Asn His Lys Lys Phe Leu Leu Leu Pro
            20                  25                  30
Pro Val Asn Phe Thr Ile Lys Ala Thr Gly Leu Ala Gln Val Leu Leu
            35                  40                  45
His Trp Asp Pro Asn Pro Asp Gln Glu Gln Arg His Val Asp Leu Glu
        50                  55                  60
Tyr His Val Lys Ile Asn Ala Pro Gln Glu Asp Glu Tyr Asp Thr Arg
65                  70                  75                  80
Lys Thr Glu Ser Lys Cys Val Thr Pro Leu His Glu Gly Phe Ala Ala
                85                  90                  95
Ser Val Arg Thr Ile Leu Lys Ser Ser His Thr Thr Leu Ala Ser Ser
```

|     |     |     |     |     | 100 |     |     |     |     | 105 |     |     |     |     | 110 |     |
|---|---|---|---|---|---|---|---|---|---|---|---|---|---|---|---|---|
| Trp | Val | Ser | Ala | Glu | Leu | Lys | Ala | Pro | Pro | Gly | Ser | Pro | Gly | Thr | Ser |
|     |     | 115 |     |     |     | 120 |     |     |     | 125 |     |     |     |     |     |
| Val | Thr | Asn | Leu | Thr | Cys | Thr | His | Thr | Val | Val | Ser | Ser | His | Thr |
|     | 130 |     |     |     |     | 135 |     |     |     | 140 |     |     |     |     |
| His | Leu | Arg | Pro | Tyr | Gln | Val | Ser | Leu | Arg | Cys | Thr | Trp | Leu | Val | Gly |
| 145 |     |     |     |     | 150 |     |     |     |     | 155 |     |     |     |     | 160 |
| Lys | Asp | Ala | Pro | Glu | Asp | Thr | Gln | Tyr | Phe | Leu | Tyr | Tyr | Arg | Phe | Gly |
|     |     |     |     | 165 |     |     |     | 170 |     |     |     |     | 175 |     |
| Val | Leu | Thr | Glu | Lys | Cys | Gln | Glu | Tyr | Ser | Arg | Asp | Ala | Leu | Asn | Arg |
|     |     |     | 180 |     |     |     | 185 |     |     |     |     |     | 190 |     |
| Asn | Thr | Ala | Cys | Trp | Phe | Pro | Arg | Thr | Phe | Ile | Asn | Ser | Lys | Gly | Phe |
|     |     | 195 |     |     |     |     | 200 |     |     |     |     | 205 |     |     |
| Glu | Gln | Leu | Ala | Val | His | Ile | Asn | Gly | Ser | Ser | Lys | Arg | Ala | Ala | Ile |
|     | 210 |     |     |     |     | 215 |     |     |     |     | 220 |     |     |     |
| Lys | Pro | Phe | Asp | Gln | Leu | Phe | Ser | Pro | Leu | Ala | Ile | Asp | Gln | Val | Asn |
| 225 |     |     |     |     | 230 |     |     |     |     | 235 |     |     |     |     | 240 |
| Pro | Pro | Arg | Asn | Val | Thr | Val | Glu | Ile | Glu | Ser | Asn | Ser | Leu | Tyr | Ile |
|     |     |     |     | 245 |     |     |     |     | 250 |     |     |     |     | 255 |     |
| Gln | Trp | Glu | Lys | Pro | Leu | Ser | Ala | Phe | Pro | Asp | His | Cys | Phe | Asn | Tyr |
|     |     |     | 260 |     |     |     |     | 265 |     |     |     |     | 270 |     |
| Glu | Leu | Lys | Ile | Tyr | Asn | Thr | Lys | Asn | Gly | His | Ile | Gln | Lys | Glu | Lys |
|     |     | 275 |     |     |     |     | 280 |     |     |     |     | 285 |     |     |
| Leu | Ile | Ala | Asn | Lys | Phe | Ile | Ser | Lys | Ile | Asp | Asp | Val | Ser | Thr | Tyr |
|     |     | 290 |     |     |     | 295 |     |     |     |     | 300 |     |     |     |
| Ser | Ile | Gln | Val | Arg | Ala | Ala | Val | Ser | Ser | Pro | Cys | Arg | Met | Pro | Gly |
| 305 |     |     |     |     | 310 |     |     |     |     | 315 |     |     |     |     | 320 |
| Arg | Trp | Gly | Glu | Trp | Ser | Gln | Pro | Ile | Tyr | Val | Gly | Lys | Glu | Arg |
|     |     |     |     | 325 |     |     |     |     | 330 |     |     |     |     | 335 |

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Trp Gly Glu Trp Ser Gln Pro Ile Tyr Val Gly Lys
1              5                       10

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CCHACGTATA THGGCTGHGA CCACTCHCCC CA 32

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

CCHACGTAAA THGGCTGHGA CCACTCHCCC CA 32

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

CCHACATAGA THGGTTGHGA CCATTCHCCC CA 32

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

CCHACGTATA THGGCTGACT CCACTCHCCC CA 32

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

CCHACGTAAA THGGCTGACT CCACTCHCCC CA 32

( 2 ) INFORMATION FOR SEQ ID NO:10:

( i ) SEQUENCE CHARACTERISTICS:
   ( A ) LENGTH: 32 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CCHACATAGA THGGTTGGCT CCATTCHCCC CA           32

( 2 ) INFORMATION FOR SEQ ID NO:11:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

His Val Asp Leu Glu Tyr His Val
   1               5

( 2 ) INFORMATION FOR SEQ ID NO:12:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

ACATGATATT CTAAATCHAC ATG           23

( 2 ) INFORMATION FOR SEQ ID NO:13:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

ACGTGGTACT CCAAGTCHAC GTG           23

( 2 ) INFORMATION FOR SEQ ID NO:14:

( i ) SEQUENCE CHARACTERISTICS:
      ( A ) LENGTH: 23 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

ACATGATATT CHAGATCHAC ATG                23

( 2 ) INFORMATION FOR SEQ ID NO:15:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

ACGTGGTACT CHAGGTCHAC GTG                23

( 2 ) INFORMATION FOR SEQ ID NO:16:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

AATTCGCGGC CGCTTTTTTT TTTTTTTT              28

( 2 ) INFORMATION FOR SEQ ID NO:17:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

CTTTAGAGCA CA                               12

( 2 ) INFORMATION FOR SEQ ID NO:18:

( i ) SEQUENCE CHARACTERISTICS:
( A ) LENGTH: 8 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

CTCTAAAG                                                                                      8

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

CATAGACACG ACAGACACGG                                                                          20

( 2 ) INFORMATION FOR SEQ ID NO:20:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

TACTGCAGAT CCGCCTCTTG AGAACCCCAC AT                                                            32

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

AAGCTTGGAT CCATGATCAT CGTGGCGCAT                                                               30

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO -continued ( i v ) ANTI-SENSE: NO ( x i ) SEQUENCE DESCRIPTION: SEQ ID NO:22:

GAGCTCACCG GATCCGCCTC TTGAGAACCC CACAT     35

CHIMERIC INTERLEUKIN 5-RECEPTOR/IMMUNOGLOBULIN POLYPEPTIDES

This is a division of application Ser. No. 07/947,130, filed Sep. 16, 1992, now U.S. Pat. No. 5,455,337.

FIELD OF THE INVENTION

The invention is directed to polypeptides and a DNA sequence coding for a fragment of one or both of the α-and/or β-chain of the human interleukin-5 receptor and coding for the constant domains of a heavy—or a light-chain of a human immunoglobulin, or a fragment thereof.

BACKGROUND OF THE INVENTION

Interleukin-5 (IL-5 or IL5) is a lymphokine secreted by T cells and mast cells and biologically activates B cells and eosinophils. The activity on B cells seems to be restricted to the murine system. No detectable activity can be found in a panel of human B-cell activation or differentiation assays. [Clutterbuck et al., Eur. J. Immunol. 17, 1743–1750 (1987)].

In murine hematopoiesis, IL-5 is a selective signal for the proliferation and differentiation of the eosinophilic lineage [Yamaguchi et al., J. Exp. Med. 167, 43–56 (1988)]. In this respect, IL-5 function shows analogies with colony-stimulating factors for other myeloid lineages. Also, human (h) IL-5 is very potent in the activation of human eosinophils [Lopez et al., J. Exp. Med. 167, 219–224 (1988); Saito et al., Proc. Natl. Acad. Sci USA 85, 2288–2292)]. A good discussion of the roles of IL-5 and eosinophils in disease is provided by Sanderson, C. J., Blood, Vol. 79, No. 12 (June 15), 1992, pp. 3101–3109.

Interleukin 5 mediates its activity through a cell membrane receptor-complex. This complex has been characterized physicochemically in both the murine and human system. Mouse pre B cell lines depending on IL5 for their growth have been developed from bone marrow and are used for IL5-receptor analysis [Rolink et al., J. Exp. Med. 169, 1693–1701 (1989)]. The human IL5-receptor (hIL-5R) can be studied on a subclone of the promyelocytic cell line HL60 induced towards eosinophil differentiation [Plaetinck et al., J. Exp. Med. 172, 683–691 (1990)].

Eosinophilic differentiation is initiated using sodium butyrate. Only high affinity (Kd=30 pM) IL5 binding sites can be found on these cells. However cross-linking studies reveal the presence of two polypeptide chains of the receptor involved in IL5 binding, with molecular masses closely resembling the murine IL5R-α-and-β chains.

Increased half-life in vivo has been shown for example, for chimeric polypeptides consisting of the first two domains or parts thereof of the human CD4-molecule and different domains of the constant regions of the heavy chain or the light chain, of amammalian immunoglobulin (see Traunecker et al., Nature 331, 84–86 [1988] and European Patent Application 90107393.2, Publication No. 394,827).

The specification of European Patent Application 90107393.2, which is the relevant portions of which are described latter in the specification, contains data with respect to the use of pSV-2-derived vectors for the expression of chimeric proteins as well as the construction of vectors for the expression of such chimaeric proteins with other immunoglobulin fragments.

As described above, sources for DNA sequences coding for constant domains of human immunoglobulins are known in the state of the art and disclosed, for example, in EP 394,827 or are described for example by Ellison et al., Nucl. Acid Res. 10, 4071–4079 (1982) for IgG1, or Huck et al., Nucl. Acid Res. 14, 1779–1789 (1986) for IgG3.

SUMMARY OF THE INVENTION

The invention is directed to a DNA sequence which comprises a combination of two DNA subsequences, with one of the subsequences coding for a fragment of the α-and/or β-chain of the hIL5R. The hIL5R fragment, or combination of fragments, is capable of binding hIL-5, and the other subsequence codes for part or all constant domains of the human immunoglobulin heavy—or light-chains.

The invention additionally pertains to vectors comprising such DNA sequences, especially such vectors capable of expression in eukaryotic host cells. The invention also relates to prokaryotic or eukaryotic host cells transformed with such vectors.

The present invention is also concerned with the recombinant chimeric polypeptides coded by such DNA sequences, as well as their use, especially for the treatment of illnesses having demonstrated eosinophilia, for example chronic asthma, and helminth infections. A soluble human IL5Rα-chain (shIL5Rα) would be advantageous as an IL-5 antagonist in chronic asthma or other disease states with demonstrated eosinophilia. In addition the shIL5Rα or the α-chain itself or the whole high affinity receptor, consisting of the α-chain and the β-chain [Tavernier et al., Cell 66, in press (1991)] could be used as a tool for screening for IL-5 antagonists. Of course, the invention also includes such proteins in which the amino acid sequences are deleted or exchanged, so that the activity of the proteins is not significantly altered. Amino acid exchanges in proteins and peptides which do not generally alter the activity of such molecules are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Ash, Leu/Ile, Leu/Val, Ala/Glu, Asp/Gly as well as these in reverse.

DETAILED DESCRIPTION OF THE INVENTION

The invention is directed, in part, to a DNA sequence which comprises a combination of two DNA subsequences, with one of the subsequences coding for a fragment of the α-and/or the β-chain of the hIL5R. The hIL5R fragment, or combination of fragments, is capable of binding hIL5, and whereby a fragment of the soluble hIL5Rα-chain (shIL5Rα) and especially such a fragment with the whole or a part of the sequence as shown in SEQ ID NO: 1 is preferred. The other subsequence codes for constant domains of the human immunoglobulin heavy—or light-chains. The heavy chains, especially all domains except the first domain of the constant domain of human immunoglobulins such as IgG, IgA, IgM or IgE and specifically IgG, for example IgG1 and IgG3 are preferred.

Figure 1:
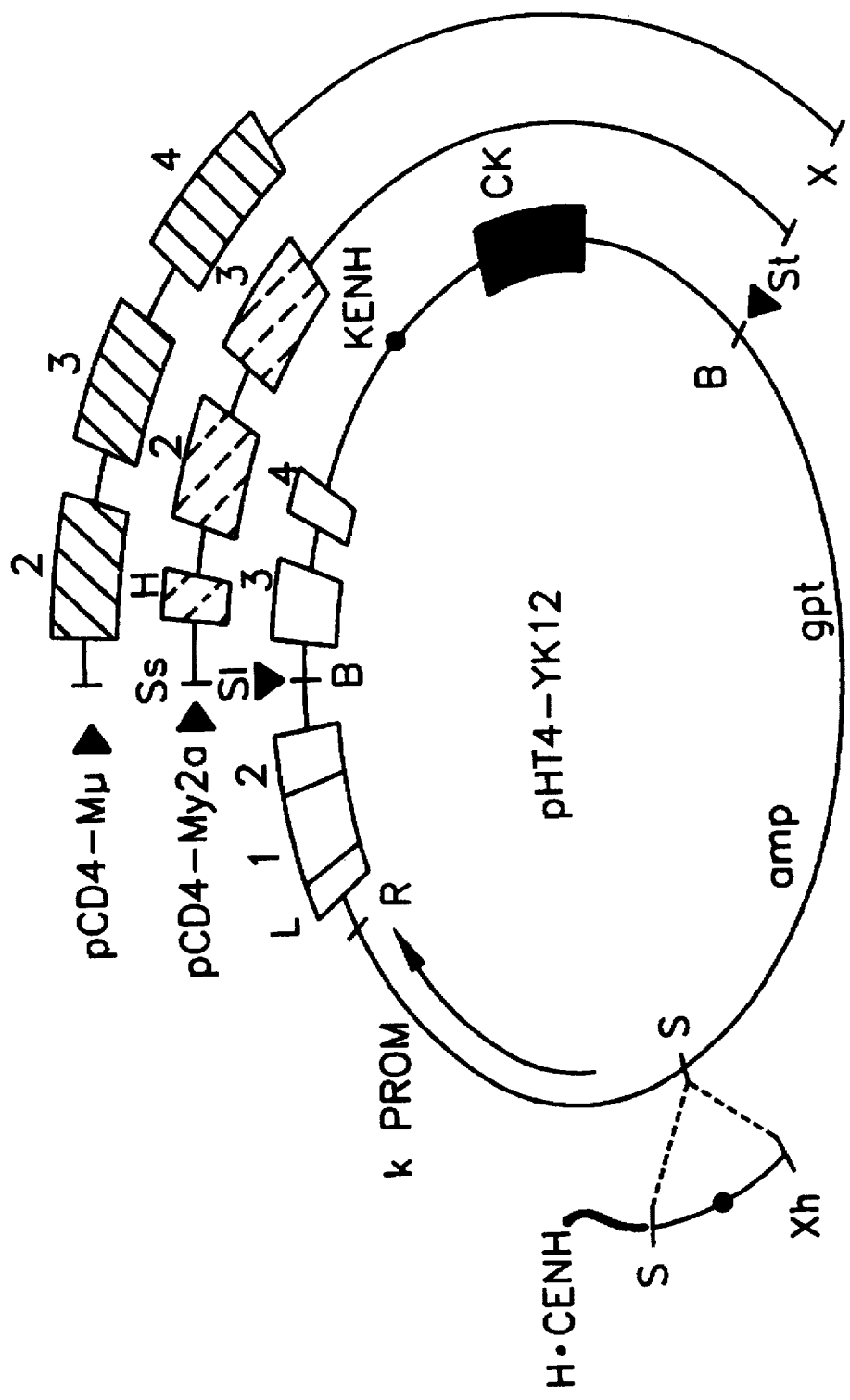
FIG. 1 shows the plasmids pHT4-YK12, pCD4-Mμ and pCD4-Mλ2a. Boxes refer to pieces of cDNA equivalent to specific parts of exons [see Example 14] or exons themselves used for the construction of the plasmids wherein the white boxes refer to DNA coding for the leader region (L) and all four (1,2,3,4) extracellular domains of the human CD4-molecule. The black box refers to the exon coding for the immunoglobulin κ light-chain constant region (cκ). The dotted boxes refer to the exons coding for the hinge (H) and the second and third domains of the mouse IgG$_{2a}$ constant regions (C2, C3) respectively. The striped boxes refer to the exons coding for the second, third and fourth domains for the mouse IgM constant regions respectively. Further abbreviations refer to: B=BamHI restriction site, R=EcoRI restriction site, S=SalI restriction site, Ss=SstI restriction site, St=StuI restriction site, X=XbaI restriction site, Xh=XhoI restriction site, amp=ampicillin resistance gene, gpt=*E. Coli* xanthine-guanine phosphoribosyltransferase gene, κ prom= Igκ promotor, κENH=Igκ enhancer, H.CENH=Ig heavy chain enhancer.

It is furthermore understood that a DNA sequence coding for a fragment of the α-chain of the hIL5R which fragment binds hIL5 comprises also DNA sequences which hybridize under stringent hybridization conditions to a DNA sequence as shown in SEQ ID NO:1 which DNA sequence codes for a protein which is capable of binding hIL5. A man skilled in the art will easily be able to define such stringent hybridization conditions based on the DNA-sequence shown in FIG. 1 and according to standard knowledge in the state of the art and disclosed for example in Sambrook et al. "Molecular Cloning", 2nd. ed., Cold Spring Harbor Laboratory Press (1989). The DNA sequences of the invention also comprise DNA sequences which hybridize to the DNA sequence which is complementary to the DNA sequence shown in SEQ ID NO:1. In addition, the DNA sequence which codes for a fragment of the α-chain of the hIL5R fragment which fragment is capable of binding hIL5 also comprises DNA sequences which, because of the degeneracy of the genetic code, do not hybridize with the sequence of SEQ ID NO:1, or its complement, but which code for polypeptides having exactly the same amino acid sequence as the fragment of the α-chain of the human IL5R.

It is furthermore understood that for the purpose of the present invention the chimeric polypeptides can be in a dimeric form, namely consisting either of two subunits whereby each subunit comprises a fragment of the α-chain of the IL5R which binds hIL5 or of two subunits whereby one of the two subunits comprises a fragment of the α-chain of the IL5R and the other subunit comprises a fragment of the β chain of the IL5R so that the dimeric polypeptide binds hIL5.

Cloned DNA can be obtained in the form of genomic DNA isolated from a genomic library by methods well known in the art and described for example by Maniatis, T., et al. in "Molecular Cloning." For example, specific oligonucleotide probes can be prepared on the at least partial knowledge of the amino acid sequence encoded by the specific genomic DNA (exons) to be isolated or the at least partial knowledge of its nucleic acid sequence. Such sequence information can be obtained in principle from any sequence data base, for example, Genbank (Intelligenetics, California, USA), EMBL (Heidelberg, FRG), NBRF (Georgetown University, Medical Centre, Washington, D.C., USA) and Vecbase (University of Wisconsin, Biotechnology Centre, Madison, Wis., USA), or more specifically, for example, for the human Ig μ from Rabbits, T. H., et al., *Nucleic Acids Res.*, 9:4509–4524 (1981); for the human IgY1 from Ellison, J. W., et al., *Nucleic Acids Res.*, 10:4071–4079 (1982); for the human Ig λ3 heavy chain gene from Huch, S., et al., *Nucleic Acids Res.*, 14:1779–1789 (1986); and for the human Igα1 and Igα2 heavy chain gene from Flanagan, J. G., et al., *Cell*, 36:681–688 (1984).

The cloning of a DNA sequence coding for the α-chain of the hIL5R can be achieved in the following manner. Murine cell lines which contain the murine IL-5-receptor (mIL5R) in membrane-bound form, can be cultivated according to methods known in the art or as specifically described, for example, in Example 2. Such cells can then be harvested by centrifugation, lysed and a membrane extract can be prepared by using a suitable detergent, for example Triton-X-100. For the isolation of the α-chain of mIL5R, the membrane extract, cleared by centrifugation, can be passed over an immunoaffinity matrix. The corresponding antibodies for such an immunematrix namely the ones to the α-chain of the mIL5R can be prepared and coupled to an appropriate matrix by methods well known in the art or as specifically described, for example, in Examples 1–3. The α-chain of the mIL5R can be further purified by sodium dodecylsulfate polyacrylamide gelelectrophoresis (SDS-PAGE) and blotted to an appropriate matrix.

The thus-purified murine IL-5-receptor chain can be characterized by methods of peptide chemistry which are known in the state of the art, such as, for example, N-terminal amino acid sequencing or enzymatic as well as chemical peptide cleavage. Fragments obtained by enzymatic or chemical cleavage can be separated according to usual methods such as, for example, HPLC and can themselves be subjected to further N-terminal sequencing.

Starting from the so-obtained amino acid sequence information, oligonucleotides can be produced according to methods known in the state of the art [see, for example, Sambrook et al., supra] taking into consideration the degeneration of the genetic code.

cDNA or genomic DNA libraries can be produced according to methods known in the art [Sambrook et al., supra.], whereby cDNA libraries on the basis of an mRNA-preparation from cell lines expressing with or without induction murine or human IL5R, for example as specifically described in Example 4, are preferred. Such libraries can then be screened by oligonucleotides [Sambrook et al., supra]. Once a specific clone has been identified in such a manner, the phage harboring the desired DNA sequence of the invention can be isolated [Sambrook et al., supra] and the corresponding inserts characterized by restriction enzyme cleavage pattern analysis or sequencing according to standard procedures [Sambrook et al., supra]. It is understood that DNA sequences hybridizing under stringent hybridization conditions to those of the present invention and coding for proteins which bind IL5 can be employed for the purpose of the present invention. Such DNA sequences can be prepared for example by mutagenesis methods known in the art [see, for example, Sambrook et al., supra] starting from the corresponding non-mutated DNA sequences. Furthermore, the well-known polymerase chain reaction (PCR) can be used for the preparation of DNA sequences of the present invention as described in detail in examples 12 and 13. Stringent hybriditation conditions can be determined by a man skilled in the art by standard procedures as given, e.g. by [Sambrook et al., supra].

On the basis of the thus-determined DNA sequences and of the already known DNA sequences for certain receptors, those partial DNA sequences which code for a soluble receptor subunit can be determined and cut out from the complete DNA sequence using known methods, see Sambrook et al., supra and Maliszewski and Fanslow, Tibtech., 8, 324–329 (1990).

The complete DNA sequence or such partial DNA sequences can then be integrated using known methods into expression vectors described in the state of the art for their amplification and/or expression in prokaryotes [Sambrook et al., supra]. Suitable prokaryotic host organisms are, for example, gram-negative and gram-positive bacteria such as, for example, B. subtilis strains or E. coli strains such as E. coli HB 101 [ATCC No; 33 694] or E. coli W3110 [ATCC No. 27 325] and E. coli MC1061 [Casadabam and Cohen, J. Mol. Biol. 138, 179–207 (1980)]. The latter two harboring plasmid "p3" [Sambrook et al., supra] in case the pCDM8-type vectors like πV X or pshIL5Rα (see Example 9) will be amplified.

Furthermore such DNA sequences can be integrated using known methods into suitable vectors for expression in eukaryotic host cells, such as, for example, yeast, insect cells and mammalian cells.

A typical expression vector for mammalian cells contains an efficient promoter element in order to produce a good transcription rate of the DNA. Also included in the vector is the DNA sequence to be expressed, and DNA coding signals for an efficient termination and polyadenylation of the transcript. Additional elements which can be used are "enhancers" which lead to again intensified transcription, and sequences which for example can bring about a longer half life of the mRNA. For the expression of nucleic acid sequences in which the endogenous sequence fragment coding for a signal peptide is missing, there can be used vectors which contain such suitable sequences which code for signal peptides of other known proteins. See, for example, the vector pLJ268 described by Cullen, B. R. in Cell 46, 973–982 (1986) as well as Sharma, S. et al. in "Current Communications in Molecular Biology", edt. by Gething, M. J., Cold Spring Harbor Lab. (1985), pages 73–78.

Most of these vectors which are used for a transient expression of a particular DNA sequence in mammalian cells contain the replication origin of the SV40 virus. In cells which express the T-antigen of the virus (for example COS cells), these vectors are reproduced abundantly. A transient expression as described for example in Example 10 is, however, not limited to COS cells. In principle, any transfectable mammalian cell line can be used for this purpose. Signals-which can bring about a strong transcription are for example the early and late promoters of SV40, the promoter and enhancer of the "major immediate-early" gene of HCMV (human cytomegalovirus), the LTR's ("long terminal repeats") of retroviruses such as, for example, RSV, HIV and MMTV. There can, however, also be used signals of cellular genes such as for example the promoters of the actin and collagenase genes.

Alternatively, however, stable cell lines which have the specific DNA sequence integrated into the genome (chromosome) also are suitable. For this, the DNA sequence is cotransfected together with a selectable marker, for example neomycin, hygromycin, dihydrofolate reductase (dhfr) or hypoxanthin guanine phosphoribosyl transferase (hgpt) using methods which are per se known in the art. The DNA sequence stably incorporated in the chromosome can also be amplified abundantly. A suitable selection marker for this is, for example, dihydrofolate reductase (dhfr). Mammalian cells, for example, chinese hamster ovary (CHO) cells, which contain no intact dhfr gene, are thereby incubated with increasing amounts of methotrexate after transfection has been effected. In this manner cell lines which contain more than a thousand copies of the desired DNA sequence can be obtained.

Mammalian cells which can be used for expression are for example cells of the human cell lines Hela [ATCC CCL2] and 293 [ATCC CRL 1573] as well as 3T3 [ATCC CCL 163] and L cells, for example [ATCC CCL 149], (CHO) cells [ATCC CCL 61], BHK [ATCC CCL 10] cells as well as the CV 1 [ATCC CCL 70] and the COS cell lines [ATCC CRL 1650, CRL 1651].

Suitable expression vectors include, for example, vectors such as pBC12MI [ATCC 67 109], pSV2dhfr [ATCC 37 146], pSVL [Pharmacia, Uppsala, Sweden], pRSVcat [ATCC 37 152], pMSG [Pharmacia, Uppsala, Sweden] and pCDM8 type plasmids like for example pshIL5Rα [see Example 7] which has been deposited transformed in E.coli MC1061 (harboring plasmid p3) under the conditions of the Budapest Treaty for patent purposes at the Deutsche Sammlung von Mikroorganismen und Zellkulturen GmbH (DSM) in Braunschweig, Federal Republic of Germany on Apr. 17, 1991 under accession number DSM 6479. The plasmid pshIL5Rα can be isolated from the deposited transformed E.coli as known in the art and described for example in detail in Example 9.

For the expression of the chimeric polypeptides of the present invention, there can be used pSV2-derived vectors [see for example German, C. in "DNA Cloning" Vol. II., edt. by Glover, D. M., IRL Press, Oxford, 1985] like pCD4-Hμ (DSM 5315), pCD4-Hλ1 (DSM 5314) and pCD4-Hλ3 (DSM 5523) which have been deposited at the Deutschen Sammlung von Mikro-organismen und Zellkulturen GmbH (DSM) in Braunschweig, FRG, and which are described in detail in European Patent Application No. 90107393.2, Publication No. 394,827. For the purpose of the present invention, the CD4 coding part in the vectors of the EPA application must be replaced by a DNA sequence coding for a fragment of the α-and/or β-chain of the hIL5R which binds hIL5. The replacement of the CD4 region with the hIL5R fragment is performed by methods known per se in the art and described for example in Sambrook et al., supra. If desirable, the specific immunoglobulin coding region in the vectors obtained also can be replaced by a DNA sequence coding for the desired immunoglobulin. Preferred vectors for the expression of the chimeric polypeptides of the present invention are pCDM8 type vectors like for example pshIL5Rα for the expression of fragments of the α-chain of the IL5R containing chimeric polypeptides (see examples 12 and 13).

The manner in which these cells are transfected depends on the chosen expression system and vector system. An overview of these methods is to be found, for example, in Pollard et al., "DNA Transformation of Mammalian Cells" in "Methods in Molecular Biology", Nucleic Acids Vol. 2, 1984, Walker, J. M., ed, Humana, Clifton, N.J. Further methods are to be found in Chen and Okayama "High-Efficiency Transformation of Mammalian Cells by Plasmid DNA", Molecular and Cell Biology 7, 2745–2752, 1987 and in Felgner Felgner et al., "Lipofectin: A highly efficient, lipid-mediated DNA-transfection procedure", Proc. Nat. Acad. Sci. USA 84, 7413–7417, 1989.

The baculovirus expression system, which has already been used successfully for the expression of a series of proteins (for an overview see Luckow and Summers, Bio/

Technology 6, 47–55, 1988), can be used for the expression in insect cells. Recombinant proteins can be produced in authentic form or as fusion proteins. The thus-produced as proteins can also be modified such as, for example, glycosylated (Smith et al., Proc. Nat. Acad. Sci. USA 82, 8404–8408, 1987). For the production of a recombinant baculovirus which expresses the desired protein there is used a so-called "transfer vector". Under this there is to be understood a plasmid which contains the heterologous DNA sequence under the control of a strong promoter, for example that of the polyhedron gene, whereby this is surrounded on both sides by vital sequences. The transfer vector is then transfected into the insect cells together with DNA of the wild type baculovirus. The recombinant viruses which result in the cells by homologous recombination can then be identified and isolated according to known methods. An overview of the baculovirus expression system and the methods used therein is to be found in Luckow and Summers, "A Manual of Methods for Baculovirus Vectors and Insect Cell Culture Procedures", Texas Agricultural Experimental Station, Texas A & M University, Bulletin No. 1555, 2nd edition, 1988. It is understood that for the practice of the present invention when using the baculovirus expression system, DNA-sequences coding for the immunoglobulin part have to be in the form of a cDNA.

The chimeric polypeptides of the invention can then be purified from the cell mass or the culture supernatants according to methods of protein chemistry which are known in the state of the art, such as, for example, precipitation for example with ammonium sulfate, dialysis, ultrafiltration, gelfiltration, ion-exchange chromatography, SDS-PAGE, isoelectric focusing, affinity chromatography-like immunoaffinity chromatography, HPLC in normal or reverse phase systems or the like.

The chimeric polypeptides of the invention as well as their physiologically compatible salts, which can be manufactured according to methods which are known in the state of the art, can also be used for the treatment of illnesses in which IL-5 is involved in their course and/or the production of corresponding pharmaceutical preparations. For this purpose, one or more of the compounds, where desired or required in combination with other pharmaceutically active substances, can be processed in a known manner with the usually used solid or liquid carrier materials. The dosage of such preparations can be effected having regard to the usual criteria in analogy to already used preparations of similar activity and structure. Such pharmaceutical preparations and the use of the compounds of the present invention for therapeutical purposes are also an object of the present invention.

The following Examples are intended to illustrate details of the invention, without thereby limiting it in any manner. Unless indicated otherwise, the Examples were carried out as written. Unless indicated otherwise, all methods used below are standard methodology according to Sambrook et al. (1989), Molecular Cloning. A Laboratory Manual (2nd edn). Cold Spring Harbor, N.Y., Cold Spring Harbor Laboratory Press.

EXAMPLE 1

Production of Monoclonal Antibodies against the Murine IL5R

Immunization was carried out generally as described by A. Rolink et al., J. Exp. Med., 169, 1693–1701 (1989). That is, at day 0, $2 \times 10^7$ B13 cells (Rolink et al., supra) were washed with phosphate buffered as saline (PBS-A), mixed with complete Freund's adjuvant (CFA) and injected into the hind footpath of Wistar rats. This was repeated without Freund's adjuvant (FA) on day 5 and 7. On day 8, regional lymph nodes were removed and a cell suspension was prepared. These cells were fused using PEG 1500 (Boehringer) with Sp2/0-Ag14 cells [ATCC CRL 1581] at a ratio of 5:1.5. Cells were plated in microtiterplates in the presence of 500 pg/ml of recombinant hIL-6 [Haegemann et al., Europ. J. Biochem. 159, 625–632 (1986)]. The next day, the same volume of medium containing a 2X conc. of aminopterin was added for selection of hybrid cells. Cells were refed at day 8 with medium without aminopterin. Hybridomas were selected on the ability of their supernatant to inhibit the mIL5 [Tavernier, J. et al., DNA 8, 491–501 (1989)] or a mouse interleukin-3 (mIL3) driven proliferation of B13 cells (measured by a $^3$Hdeoxy-cytidin incorporation assay as known in the art). Conditioned medium from WEHI-3 cells (ATCC No. TIB68) was used as a source of mIL3. Supernatants demonstrating inhibiting activity were retested in a competition-binding assay with radiolabeled (according to methods known in the art) mIL5 or "R52" (a monoclonal antibody recognizing only the β-chain of the IL-5-R, see Rolink et al., supra) on B13 cells. Monoclonal antibodies directed only to the α-chain of the mIL-5-R were identified on their ability to almost completely inhibit mIL5 binding and by immunprecipitation of the corresponding mIL-5-R chain. Selected hybridomas were recloned by the well-known limiting dilution method.

EXAMPLE 2

Immunoaffinity Purification of the mIL5R-β-chain

B13 cells were grown in large spinner flasks in Iscove's modified Dulbecco's medium (Gibco Laboratories, Grand Island N.Y., USA) containing 5% fetal calf serum, 2 mM L-glutamine, 50 µg/ml gentamycin, and 100 units/ml recombinant mouse IL-5, to a density of $2 \times 10_6$ cells/ml. Cells from 10 l cultures were concentrated by as centrifugation, washed with PBS and lysed in 200 ml PBS containing 1% Triton-X-100 and a cocktail of protease inhibitors (1 mM PMSF, 10 mM benzamidine. HCl, 100 U/ml aprotinin). After 10 min on ice, the lysate was centrifuged for 10 min at 1000×g and cleared by ultracentrifugation (100.000×g) for 90 min at 4° C. The supernatant was diluted with NaCl to a final concentration of 0.5M, and used for purification. "R52" was covalently bound to protein G-Sepharose 4 Fast Flow (Pharmacia, LKB Biotechnology AB, Uppsala, Sweden) according to Schneider et al.[J. Biol. Chem. 257, 10766 (1982)], at a concentration of 5 mg/ml gel. Two hundred ml lysate of B13 cells was passed at 4° C. as over 2 ml protein G-Sepharose 4 Fast Flow followed by 2 ml R52-linked protein G-Sepharose 4 Fast Flow both packed in a 1 cm diameter column. The flow through was then reloaded on both columns. The gel was washed extensively (100 ml) with a buffer containing 50 mM Tris-HCl (pH8.2), 1 mM EDTA, 0.5M NaCl, 0.5% NP40, followed by 10 ml 0.1% (NP40). Next, the retained proteins were eluted in 4 ml 50 mM diethylamine (pH11) containing 0.1% Nonidet P40 (NP40), neutralized by addition of 1M $NaH_2PO_4$ and concentrated by lyophilization. The purity was assessed by SDS-PAGE and Coomassie staining of 2.5% of the eluate.

EXAMPLE 3

Immunoaffinity Purification of the Murine IL5R α-Chain

B13 cell lysates from $2 \times 10^{10}$ cells (run through fractions of the "R52"-immunoaffinity column used to purify the β-chain doublet according to Example 2) were mixed overnight by 4° C. with 2 ml hydrazide avidgel AX (Bioprobe Int. Inc.) armed with 10 mg mAbs recognizing the mIL5R α-chain. The gel was then poored into a column, and after extensive washing (50 mM Tris. HCl, pH 8.2, 1 mM EDTA, 0.5M NaCl, 0.5% NP40; followed by 0.1% NP40 in $H_2O$) elution was performed using 50 mM diethylamine, pH11, 0.01% NP40. Selected fractions were immediately lyophilized and resuspended in 2x Laemmli buffer, in the presence of β-mercaptoethanol. Samples were as run through a 1.5 mm 10% PAGE-SDS gel. The gel was fixed in 10% HAc, 30% methanol and stained with Coomassie Brilliant Blue. Slices containing the 60 kDa mIL5R α-chain were treated with SDS buffer, sliced further and electrophoresed in a new PAGE-SDS gel.

After transfer to an Immobilon-P membrane (Millipore Corp.), and staining with amido black, the 60 kDa band was-excised and in situ digested with trypsin. Peptides were separated on a C4-reversed-phase column and subjected to sequence analysis using a 470A-type gas-phase sequenator equipped with an on-line 120A-type PTH-amino acid analyser (Applied Biosystems Inc., Foster City, Calif.). Amino acid sequences (standard abbreviations of amino acids) and the sequences of corresponding sets of oligonucleotide probes, synthesized according to methods known in the art, are shown below:

cDNAs were ligated into the EcoR1-Not1 arms of the λgt11 Sfi-Not vector (Promega Corp.). After in vitro packaging, around $40 \times 10^6$ recombinant phages were obtained.

2. Human, HL60 Clone (Butyrate Induced) cDNA Library

Prior to mRNA purification, butyrate induced HL60 clone 15 cells [Fischkoff, Leukemia Res. 12, 679–686 (1988); Plaetinck et al. J. Exp. Med. 172, 683–691 (1990); HL60: ATCC-No. CCL 240] were checked for proper $^{125}$I-hIL5 binding (around 2000 binding sites per cell). The same protocols as for the murine pre-B cell B13 cDNA library, above, were used, and a comparable yield of recombinant phage was obtained.

EXAMPLE 5

Screening of Murine and Human cDNA Libraries

Two sets of oligonucleotide probes "Oligonucleotide 1" and "Oligonucleotide 2", see Example 3, were used for screening under different hybridization conditions, dependent on the type of probe used, by methods known in the art [Sambrook et al., supra]. Results are presented in the scheme below:

1. Two cDNA clones (λgt11-mIL5Rα2,3) were selected from part of the murine cDNA library ($1.2 \times 10^6$ plaques were screened), on the basis of hybridization with both sets of oligonucleotide probes. For that purpose, plaque lifts were

```
peptide 1
1 2 3 4  5 6 7 8 9  10 11 12
W G E W S Q P I Y  V G K    [SEQ ID NO: 4]

oligonucleotide-set 1: 32 mers
             T                                      [SEQ ID NO: 5]
5' CC IAC GTA AAT IGG CTG IGA CCA CTC ICC CCA 3'   [SEQ ID NO: 6]
         A   G       T           T                  [SEQ ID NO: 7]

T                                      [SEQ ID NO: 8]
5' CC IAC GTA AAT IGG CTG ACT CCA CTC ICC CCA 3'   [SEQ ID NO: 9]
         A   G       T   G   T                      [SEQ ID NO: 10]

peptide 2
1 2 3 4 5 6 7 8
H V D L E Y H V      [SEQ ID NO: 11]

oligonucleotide-set 2: 23-mers
5' AC ATG ATA TTC TAA ATC IAC ATG 3'  [SEQ ID NO: 12]
      G   G   C   C   G       G       [SEQ ID NO: 13]

5' AC ATG ATA TTC IAG ATC IAC ATG 3'  [SEQ ID NO: 14]
      G   G   C       G       G       [SEQ ID NO: 15]
```

EXAMPLE 4

Construction of Unidirectional λGT11 cDNA Libraries

1. Murine Pre-B Cell B13 cDNA Library mRNA was extracted from B13 cells using the "fast-track" mRNA isolation system (Invitrogen Corp.). Using this protocol, poly(A)$^+$ mRNA was directly isolated from cell lysates using oligo(dT) cellulose; yields were around 50 μg per $10^8$ cells. 5 mg poly(A)$^+$ mRNA was reverse transcribed using an oligo dT-Not1 primer-adaptor (5'-AATTCGCGGCCGC(T)$_{15}$—3' [SEQ ID NO:16], Promega Corp.) and cloned Moloney Murine Leukemia Virus RNaseH$^-$ Reverse Transcriptase (BRL Life Technologies, Inc.). EcoR1 linkered double stranded cDNA was made using described procedures [Sambrook et al., supra]. Not1 cleavage was used to generate a unique 3' sticky-end, and cDNAs were size selected (>1.000 bp) on a 1% agarose gel. After elution using the "gene clean" protocol (BIO 101 Inc.), prepared as described using Biodyne A transfer membranes (Pall), [Sambrook et al., supra]. Oligonucleotide 1 was radioactively labeled by kinasing [Sambrook et al., supra] and was hybridized under "intermediate stringency" hybridization conditions, as described below. Oligonucleotide 2 was radioactively labeled by kinasing [Sambrook et al., supra] and was hybridized under "low stringency" hybridization conditions as described below.

2. One cDNA clone (λgt11-hIL5Rα8) was selected from part of the human cDNA library ($2.4 \times 10^6$ plaques were screened), on basis of hybridization with both "oligonucleotide 1" and the cDNA insert, which was derived by methods known in the art, from the murine λgt11mIL5Rα2.

Oligonucleotide 1 was radioactively labeled by kinasing [Sambrook et al., supra] and was hybridized under "low stringency" hybridization conditions. The cDNA insert form λgt11mIL5Rα2 was radioactively labeled by random labeling [Sambrook et al., supra] and was hybridzed under "intermediate stringency" hybridization conditions.

3. Five additional cDNA clones (λgt11-hIL5Rα11→15) were selected from half of the human cDNA library screened as in 2-above, using the mIL5Rα2 cDNA probe. Hybridization was under "intermediate stringency" conditions.

4. Thirty-six additional cDNA clones (λgt11-hIL5Rα16→51) were selected from the other half of the human cDNA library screened as in 2above using the hIL5Rα8-cDNA probe. Hybridization was under "high stringency" conditions as described below.

Hybridization Conditions

"Low Stringency" Hybridization Conditions:
prehybridization: 5×SSC (citrate buffered salt solution known in the art, see for example Sambrook et al.), 5x Denhardt's, 0.1% SDS, 0.05% sodium pyrophosphate, 100 µg/ml sonicated salmon sperm DNA; overnight at 42° C.
hybridization: prehybridization buffer was replaced by the same buffer but including the radioactively labeled probe.
washes: 4 consecutive washes (around 30 min. each) with 2x SSC, 0.1% SDS at 37° C.:

"Intermediate Stringency" Hybridization Conditions:
prehybridization: 20% formamide, 5x SSC, 5 x Denhardt's, 5 mM EDTA, 25 mM sodium phosphate (pH 6.5), 0.05% sodium pyrophosphate, 100 µg/ml sonicated salmon sperm DNA; overnight at 42° C.
hybridization: prehybridization buffer was replaced by the same buffer but including the radioactively labeled probe.
washes: 4 consecutive washes (around 30 min. each) with 2x SSC, 0.1% SDS at 37° C.

"High Stringency" Hybridization Conditions:
prehybridization: 6x SSC, 5x Denhardt's, 0.5% SDS, 100 µg.ml$_{-1}$, sonicated salmon sperm DNA, overnight at 68° C.
hybridization: 6x SSC, 5x Denhardt's, 0.5% SDS, 5 mM EDTA, 100 µg.ml$^{-1}$ sonicated salmon sperm DNA including the radioactively labeled probe.
washes: the following consecutive washes (around 30 min. each) were performed: −2x SSC, 0.1% SDS at room temperature (twice); and 0.1x SSC, 0.1% SDS at 68° C. (twice).

EXAMPLE 6

Sequencing

All cDNAs were subcloned in pGEM7zf type vectors (Promega Corp.), and Exo III deletion mutants have been generated according to methods known in the art. Sequencing was performed using a protocol based on the Sanger procedure and involving Taq polymerase and single stranded DNA on an automated 370A DNA Sequencer.

EXAMPLE 7

Construction of Plasmid "pshIL5Rα"

Plasmid constructions were carried out as described in the following paragraphs. Unless indicated otherwise, all methods used below are standard methodology according to Sambrook et al. (1989), Molecular Cloning. A Laboratory Manual (2nd edn). Cold Spring Harbor, N.Y., Cold Spring Harbor Laboratory Press.

The insert from phage λgt11-hIL5Rα12 (see Example 5) was excised using EcoR1 and Not1 restriction enzymes. Both sticky ends were filled in using E.coli DNA polymerase 1 Klenow fragment in the presence of all four deoxynucleotide triphosphates, and non-palindromic BstX1 linkers were added using T4 DNA ligase. The sequence of these linkers is as follows:

5'CTTTAGAGCACA 3'[SEQ ID NO:17]
3'GAAATCTC5'. [SEQ ID NO:18]

In the next step, the modified insert was ligated into plasmid pCDM8, see., Seed and Aruffo, Proc. Natl. Acad. Sci. USA, 84, 3365 (1987); Aruffo and Seed, Proc. Natl. Acad. Sci. USA, 84, 8573 (1987); and Seed, Nature, 329, 840 (1987); and the construct with the appropriate orientation versus the CMV-promoter was chosen for further analysis.

EXAMPLE 8

Transformation of E.coli MC1061(p3)

Transformation of E.coli MC1061 (p3) with the plasmid pshIL5Rα of Example 7 was achieved by the electropotation procedure. A Gene Pulser from Bio-Rad (Richmond, Calif., USA) was used in accordance with manufacture's instructions, with settings at: 25 µF, 2.5 kV and 200 Ohms.

EXAMPLE 9

Isolation of Plasmid DNA

Plasmid DNA from transformed E.coli MCI061, as described in Example 8, was prepared using a standard procedure Birnboim and Doly, Nucl. Acids Res. 7, 1513 (1979); and Sambrook et al., 1989) based upon alkali lysis of the cells, followed by a cesium-chloride ultracentrifugation step. In this way plasmid pshIL5Rα was separated from plasmid p3. The insert coding for shIL5Rα was cut out of pshIL5Rα and sequenced as described in Example 6. The complete nucleic acid sequence and the deduced amino acid sequence of the shIL5Rα are shown in SEQ ID NO:1 and SEQ ID NO:2, respectively. SEQ ID NO:3 is the corresponding amino acid sequence of the murine IL5Rα.

EXAMPLE 10

Expression of shIL5Rα in COS-1 cells

COS-1 cells were transfected using the DEAE-Dextran protocol as described in Sambrook et al., 1989. Subconfluent COS-1 Cells were harvested by trypsinization and replated at $2.3 \times 10^4$ cells/cm$^2$, 24 hours prior to transfection. The monolayers were washed twice with minimal essential medium (MEM)-Hepes pH 7.2 and incubated for 30 minutes with the transfection mixture [10 µg pshIL5Rα isolated as described in Example 9/0.5 mg DEAE-dextran ($M_r=2\times10^6$; Pharmacia, Uppsala, Sweden)/ml MEM-Hepes, pH 7.2]. Next the cells were supplemented with 8 volumes prewarmed Dulbecco's modified Eagles medium (DMEM) containing 10% foetal calf serum (FCS) and 100 µM chloroquine diphosphate, and incubated for 4 hours at 37° C. Thereafter the medium was removed by aspiration and the monolayers were washed once with DMEM and incubated for 3 days in DMEM+10% FCS.

EXAMPLE 11

Characterization of shILS α

Supernatant of COS-1 cells transfected with plasmid pshIL5Rα prepared as described in Example 10 was tested for the presence of secreted shIL5Rα in a competition binding assay as follows: COS-1 cells transfected as described in Example 10 with a plasmid comprising a cDNA coding for mIL5Rα (for amino acid sequence see SEQ ID NO:1), obtained from a clone as described in Example 5 and constructed as described in Example 7, were detached by treatment with phosphate buffered saline (PBS) containing 0.5 mM EDTA and 0.02% sodium azide for 30 minutes at 37° C., resuspended at 1.5 ×10$^5$ cells per 0.3 ml binding medium (DMEM+10% FCS+0.02% sodium azide) and incubated with 0.8 nM $^{125}$I-mIL5 at 4° C. for 1 hour in the absence of 100-fold excess unlabeled mIL5. Supernatant of COS-1 cells (80% of binding medium) transfected with pshIL5Rα was tested for its capacity to inhibit the binding of $^{125}$I-mIL5. Binding was also carried out in the presence of 80% supernatant of untransfected COS-1 cells. To separate cell membrane bound $^{125}$I-mIL5 from free radioactivity COS-1 cells were sedimented through a phthalate oil cushion and individual pellets were counted in a gamma counter as described, for example, see Plaetinck et al., J. Exp. Med. 172, 683–691 (1990).

EXAMPLE 12

Construction of a Chimeric Human IL5Rα-IgG1 Molecule

As a first step, a polymerase chain reaction (PCR) was performed using plasmid pshIL5Rα as a template and using the following primers:

5'-CATAGACACGACAGACACGG [SEQ ID NO:19], located in the 5' untranslated region of the hIL5Rα gene (position 104→123) and 5'-TACTGCAGATCCGCCTCTTGAGAACCCCACAT [SEQ ID NO:20, a primer which matches the last 17 residues of the coding region of the hIL5Rα soluble form, with the addition of 15 residues coding for a Gly-Gly-Ser-Ala "linker" region, and a PstI recognition site. The PCR was performed using Vent Polymerase, under conditions as described by the manufacturer (New England BioLabs Inc., Beverly, Mass., USA).

After phenol extraction and ethanol precipitation, the PCR product was resuspended in an appropriate buffer, and was kinased by T4 kinase and blunted by Klenow Polymerase by methods described.

To the blunt ended PCR fragment, Bst X1 recognition sites were added, by ligation of 2 synthetic non-palindromic oligonucleotides with the sequence 5'-CTTTAGAGCACA [SEQ ID NO:17] and

3'-GAAATCTC [SEQ ID NO:18].

The resulting fragment was then ligated into Bst X1-opened pCDM8 vector.

The resulting plasmid containing the fragment in a sense orientation relative to the CMV promotor in pCDM8 was opened by Not 1 cleavage, followed by a partial Pst1 restriction digestion. A Pst1-Eag1 restriction fragment was purified from the pBRHIG1 plasmid vector (Ellison et al.), and ligated into the plasmid vector described above.

The Eag1 and Not1 restriction enzymes generate the same sticky ends, and that fusion of both causes the loss of the Not1 recognition site, but not of the Eag1 recognition site. Hence, to favor the desired recombinant construct, a Not1 counterselection was performed.

EXAMPLE 13

Construction of a Chimeric Human IL5Rα-IgG3 Molecule

The same protocol as description in Example 12 was used with the following exceptions:

The PCR 5' linker was:

```
        Met
5'-AAGCTT GGATCCATGATCATCGTGGCGCAT  [SEQ ID NO: 21]
    Hind3  BamH1
``` which creates two extra restriction sites as indicated 5' to the nucleotides which match with the first 6 amino acids of hIL5Rα.

As PCR 3' linker the following nucleotide was used:

5'-GAGCTCACCGGATCCGCCTCTTGAGAACCCCACAT. [SEQ ID NO:22]

In addition a partial Sac1 digest was used instead of a Pst1 digest and pATHIG3(2) (Huck et al. s.a.) was used as a source of the immuno-globulin gene part.

EXAMPLE 14

Construction of Plasmids

Plasmid constructions can be carried out using standard methodology as described by Maniatis, et al., "Molecular Cloning: A Laboratory Manual," Cold Spring Harbor Laboratory, New York. (1982).

The starting plasmid for all constructions is designated pHT4-Y1 and can be prepared as previously described by Traunecker, Luke and Karjalainen in Nature, 331:84–86 (1988). This vector, carrying as selection markers the ampicillin resistance gens and the gpt gene (Mulligan and Berg, Science, 209:1422 (1980)), encodes in addition a hybrid protein composed of the whole extracellular portion of the human CD4 receptor fused to the mouse immunoglobulin kappa light-chain constant region.

Vector pHT4-Y1 was modified by replacing the mouse Ig heavy chain promoter by the more efficient mouse Ig kappa promoter derived from the vector pKm 1 (Traunecker et al., Eur. J. Immunol., 16:851–854 (1986)). The kappa promoter was first subcloned as a BglII/SalI fragment into the vector pUC18 digested with BamHI and SalI, recovered as a 2.2 kb HindIII (3' recessive ends filled with the help of the Klenow fragment of E. coli DNA polymerass, called hereafter: blunt)/EcoRI fragment and subsequently inserted into XbaI (blunt)/EcoRI digested pHT4-Y1 to generate plasmid pHT4-YK12 (see FIG. 1).

This plasmid was then digested with BamHI, to remove the exons 3 and 4 of the CD4 gens and the exon encoding the mouse Ig kappa light chain constant region, the 3' recessive ends were filled with Klenow polymerase and dephosphorylated with calf intestine alkaline phosphatase to facilitate the insertion of the following gene fragments (blunt ended before ligation):

- a 3.5 kb SstI/XbaI DNA fragment containing the constant region exons C2, C3 and C4 of the mouse Ig μ heavy chain gene [Arnheim, N., et al., Cell, 22:179–185 (1980)] resulting in the preliminary plasmid pCD4-Mμ*.
- a 3.0 kg StuI DNA fragment containing the Hinge and the C2 and C3 constant region exons of the mouse Ig γ2a heavy chain gene [Roeder, W., et al., PNAS, 78:474–479 (1981)] resulting in the preliminary plasmid pCD4-Mγ2a*.
- a HaeII DNA fragment (made blunt with T4 DNA polymerase) containing the Hinge and the C2 and C3 constant region exons of the human Igγ1 heavy chain gene [Ellison, J. W., et al., Nucleic Acids Res., 10:4071–4079 (1982)] resulting in the preliminary plasmid pCD4-Hγ1*.

a DNA fragment containing the constant region exons C2, C3 and C4 of the human Ig γ1 heavy chain gene [Rabbits, T. H., et al., *Nucleic Acids Res.*, 9:4509–4524 (1981)]. This DNA fragment was constructed as follows: first, the HaeII fragment of the human Igγ1 heavy chain gene was made blunt ended as described and inserted into a blunt ended SalI site of pUC19 in an orientation positioning the Hinge exon towards the BamHI site. This intermediate construct was then digested with PstI to remove the 3 μl exons except for the splice acceptor site of the Hinge exon flanking the PstI site in the gens (the second PstI site is in the pUC19 polylinker), followed by the insertion of the PstI fragment of the human μ gene containing exons C2, C3 and C4 (Rabbits, et al., see above). This final gens construct was then recovered by BamHI and HindIII digestion (both sites in the pUC19 polylinker), followed by Klenow treatment and insertion into vector pHT4 YK12 as described above resulting in the preliminary plasmid pCD4-Hμ*.

Figure 2:
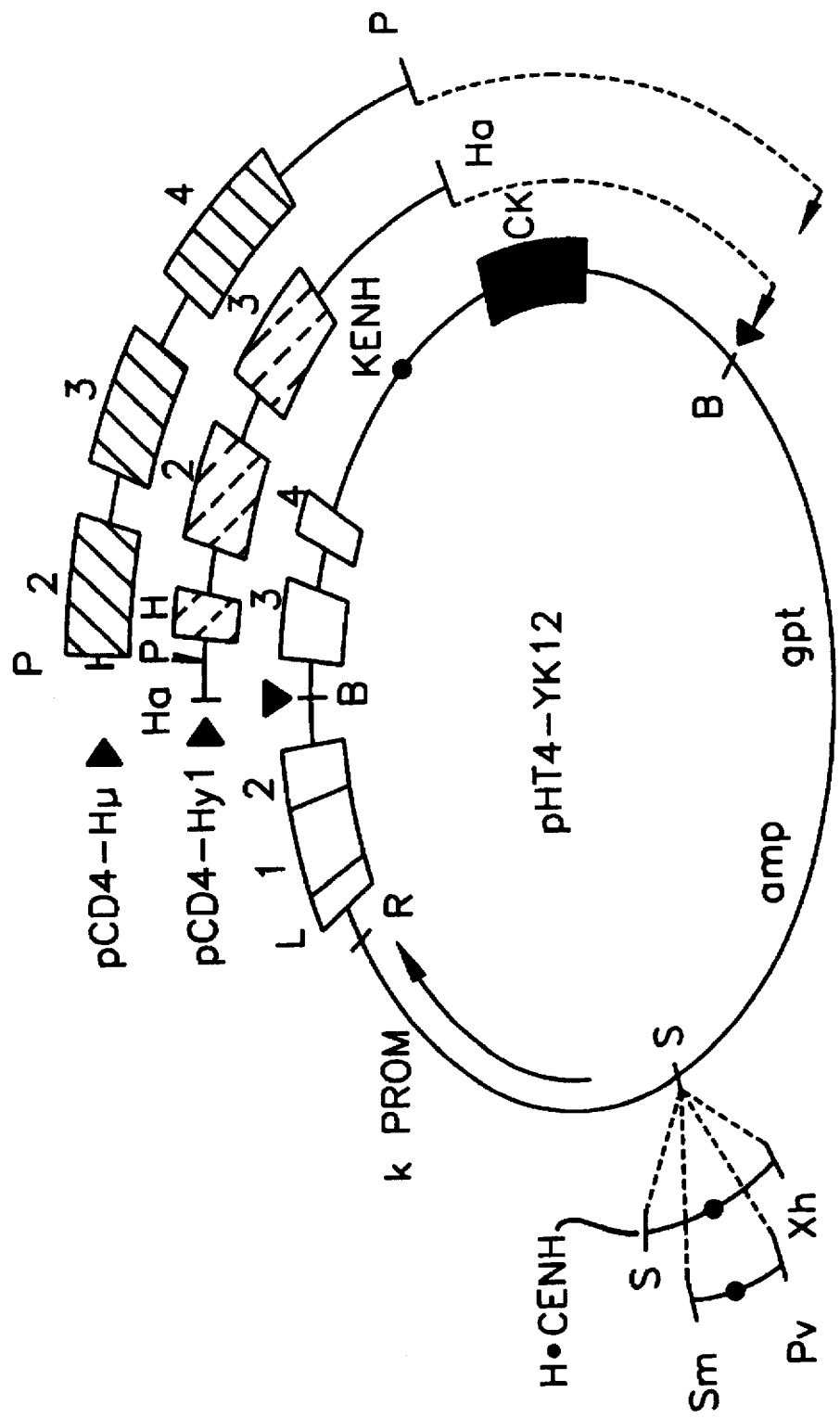
FIG. 2 shows plasmids pHT4-YK12 (see FIG. 1), pCD4-Hμ and pCD4-Hλ1. In these latter plasmids, the boxes represent the human IgG and IgM regions corresponding to the mouse exons of FIG. 1. "P" refers to a PstI restriction site and "Ha" to a HaeII restriction site, "PV" to a PVuII restriction site and "Sm" to a SmaI restriction site. All other symbols and abbreviations have the same meaning as in FIG. 1.

The preliminary plasmids (pCD4-Mμ*, pCD4-Mγ2a*, pCD4-Hγ1*) were completed by inserting a XhoI SalI fragment which contains the murine μ heavy chain gens enhancer into the unique SalI site 5' to the promoter (see FIGS. 1 and 2) and the preliminary plasmid pCD4-Hμ was completed by inserting the murine μ "core" enhancer as a SmaI-PvuII fragment into the blunt-ended SalI site 5' to the promoter (FIG. 2), resulting in the final plasmids pCD4-Mμ, pCD4-Mγ2a, pCD4-Hγ1 and pCD4-Hμ. Originally the enhancer fragment XbaI EcoRI described by Gillies, et al. (*Cell*, 33:717-728, (1983)) was inserted, via an EcoRI-linker on XbaI, into the EcoRI site of the Bluescript vector (Stratagens, La Jolla, USA) in an orientation positioning the XbaI(EcoRI) site next to the EcoRV site. Into the unique SstI site of the vector an adaptor was inserted which contained a XhoI site. Finally, the enhancer fragment was recovered with XhoI-SalI for constructs pCD4-Mμ, pCD4-Mγ2a and pCD4-Hγ1 or with SmaI-PvuII for construct pCD4-Hμ.

For the construction of pCD4-Hγ3 plasmid pHT4-YK12 (see FIG. 1) was digested with BamHI to remover the exons 3 and 4 of the CD4 gene and the exon encoding the mouse Ig kappa light chain constant region, and dephosphorylated with calf intestine alkaline phosphatase to facilitate the insertion of a 6.0 kb BglII DNA fragment containing the hinge and the C2 and C3 constant region exons of the human Igγ3 heavy chain gene [Huch, S., et al., *Nucleic Acids Res.*, 14:1779–1789 (1986)] resulting in the preliminary plasmid pCD4-Hγ3*. The preliminary plasmid pCD4-Hγ3* was completed by inserting the murine μ "cae" enhancer as described above for plasmid pCD4-Hμ.

What is claimed is:

1. An isolated DNA molecule comprising:
   (a) a first DNA subsequence encoding SEQ ID NO:2; and
   (b) a second DNA subsequence selected from the group consisting of:
      (i) a DNA subsequence encoding a constant domain of a heavy chain of a human immunoglobulin, and
      (ii) a DNA subsequence encoding a constant domain of a light chain of a human immunoglobulin.

2. The isolated DNA molecule according to claim 1, wherein:
   (a) the second DNA subsequence comprises a DNA sequence encoding a constant domain of a heavy chain of a human immunoglobulin; and
   (b) the first DNA subsequence and the second DNA subsequence are linked 5'-3'.

3. The DNA sequence according to claim 2, wherein the second DNA subsequence encodes all domains, except the first domain, of the constant region of a heavy chain of a human immunoglobulin selected from the group consisting of IgG, IgA, IgM and IgE.

4. The DNA sequence according to claim 3, wherein the human immunoglobulin is selected from the group consisting of IgM and IgG.

5. The DNA sequence according to claim 4, wherein the human immunoglobulin is IgG of the IgG1 or IgG3 type.

6. A vector comprising a DNA sequence, the DNA sequence comprising:
   (a) a DNA subsequence encoding SEQ ID NO:2; and
   (b) a second DNA subsequence selected from the group consisting of:
      (i) a DNA subsequence encoding a constant domain of a heavy chain of a human immunoglobulin, and
      (ii) a DNA subsequence encoding a constant domain of a light chain of a human immunoglobulin.

7. The vector according to claim 6, wherein:
   (a) the second DNA subsequence comprises a DNA sequence encoding a constant domain of a heavy chain of a human immunoglobulin; and
   (b) the first DNA subsequence and the second DNA subsequence are linked 5'-3'.

8. The vector according to claim 7, wherein the second DNA subsequence encodes all domains, except the first domain, of the constant region of a heavy chain of a human immunoglobulin selected from the group consisting of IgG, IgA, IgM and IgE.

9. The vector according to claim 8, wherein the human immunoglobulin is selected from the group consisting of IgM and IgG.

10. The vector according to claim 9, wherein the human immunoglobulin is IgG of the IgG1 or IgG3 type.

11. A prokaryotic or eukaryotic host cell transformed with a vector, the vector comprising a DNA sequence, the DNA sequence comprising:
    (a) a first DNA subsequence encoding SEQ ID NO:2; and
    (b) a second DNA subsequence selected from the group consisting of:
       (i) a DNA subsequence encoding a constant domain of a heavy chain of a human immunoglobulin, and
       (ii) a DNA subsequence encoding a constant domain of a light chain of a human immunoglobulin.

12. The prokaryotic or eukaryotic host cell according to claim 11, wherein:
    (a) the second DNA subsequence comprises a DNA sequence encoding a constant domain of a heavy chain of a human immunoglobulin; and
    (b) the first DNA subsequence and the second DNA subsequence are linked 5'-3'.

13. The host cell according to claim 12, wherein the second DNA subsequence encodes all domains, except the first domain, of the constant region of a heavy chain of a human immunoglobulin selected from the group consisting of IgG, IgA, IgM and IgE.

14. The host cell according to claim 13, wherein the human immunoglobulin is selected from the group consisting of IgM and IgG.

15. The host cell according to claim 14, wherein the human immunoglobulin is IgG of the IgG1 or IgG3 type.

16. An isolated DNA molecule comprising:
    (a) a first DNA subsequence which (1) encodes SEQ ID NO:2, and (2) hybridizes under high stringency conditions with the DNA sequence of SEQ ID NO:1 or its complementary strand; and
    (b) a second DNA subsequence comprising a DNA sequence encoding a constant domain of a heavy chain of a human immunoglobulin; the first DNA subsequence and the second DNA subsequence being linked 5'-3'.

17. The DNA sequence according to claim 16, wherein the second DNA subsequence encodes all domains, except the first domain, of the constant region of a heavy chain of a human immunoglobulin selected from the group consisting of IgG, IgA, IgM and IgE.

18. The DNA sequence according to claim 17, wherein the human immunoglobulin is selected from the group consisting of IgM and IgG.

19. The DNA sequence according to claim 18, wherein the human immunoglobulin is IgG of the IgG1 or IgG3 type.

20. A vector comprising a DNA sequence, the DNA sequence comprising:
    (a) a first DNA subsequence which (1) encodes SEQ ID NO:2, and (2) hybridizes under high stringency conditions with the DNA sequence of SEQ ID NO:1 or its complementary strand; and
    (b) a second DNA subsequence comprising a DNA sequence encoding a constant domain of a heavy chain of a human immunoglobulin; the first DNA subsequence and the second DNA subsequence being linked 5'-3'.

21. The vector according to claim 20, wherein the second DNA subsequence encodes all domains, except the first domain, of the constant region of a heavy chain of a human immunoglobulin selected from the group consisting of IgG, IgA, IgM and IgE.

22. The vector according to claim 21, wherein the human immunoglobulin is selected from the group consisting of IgM and IgG.

23. The vector according to claim 22, wherein the human immunoglobulin is IgG of the IgG1 or IgG3 type.

24. A prokaryotic or eukaryotic host cell transformed with a vector, the vector comprising a DNA sequence, the DNA sequence comprising:
  (a) a first DNA subsequence which (1) encodes SEQ ID NO:2, and (2) hybridizes under high stringency conditions with the DNA sequence of SEQ ID NO:1 or its complementary strand; and
  (b) a second DNA subsequence comprising a DNA sequence encoding a constant domain of a heavy chain of a human immunoglobulin; the first DNA subsequence and the second DNA subsequence being linked 5'-3'.

25. The host cell according to claim 24, wherein the second DNA subsequence encodes all domains, except the first domain, of the constant region of a heavy chain of a human immunoglobulin selected from the group consisting of IgG, IgA, IgM and IgE.

26. The host cell according to claim 25, wherein the human immunoglobulin is selected from the group consisting of IgM and IgG.

27. The host cell according to claim 26, wherein the human immunoglobulin is IgG of the IgG1 or IgG3 type.

* * * * *